United States Patent [19]

Whitten

[11] Patent Number: 4,582,940

[45] Date of Patent: Apr. 15, 1986

[54] CHEMICAL PROCESS

[75] Inventor: Charles E. Whitten, Midland, Mich.

[73] Assignee: Polaroid Corporation, Cambridge, Mass.

[21] Appl. No.: 221,619

[22] Filed: Dec. 31, 1980

[51] Int. Cl.[4] ............................................. C07C 69/74
[52] U.S. Cl. .................................... 568/346; 560/122
[58] Field of Search ......................... 560/122; 568/346

[56] References Cited

U.S. PATENT DOCUMENTS 3,690,872  9/1972  Gabrielsen .............................. 96/66

OTHER PUBLICATIONS

Ehrig et al, Chem. Ber., 108, 1961 (1975).
House, Modern Synthetic Reactions, pp. 595–615, 747–754 (1972).
Seebach et al, Angen Chemie Int. Ed., 13, 400 (1974).
Balick, et al, Pol. J. Chem., 53, 893, (1979) Abstract only.

Primary Examiner—Robert Gerstl
Attorney, Agent, or Firm—Gaetano D. Maccarone

[57] ABSTRACT

There is described a method for synthesizing 3-nitro-1,2-cyclopentanedione salts which are substituted in the 4-position with an alkyl substituent and in the 5-position with an electron withdrawing substituent. The method comprises the addition and spontaneous cyclization reaction of a nitro olefin with a pyruvate anion. The salts can be converted to the nitro diones or used as intermediates in the preparation of amino reductones.

6 Claims, No Drawings

CHEMICAL PROCESS

BACKGROUND OF THE INVENTION

This invention relates to a method for preparing salts of 3-nitro-1,2-cyclopentanediones which are substituted in the 4-position with an alkyl substituent and in the 5-position with an electron withdrawing group.

A variety of reductone compounds including amino reductones are known and a number of such compounds have been taught for use in photography. For example, U.S. Pat. No. 3,690,872 is directed to the use of certain amino hydroxy cycloalkenones as silver halide developing agents including 3-amino-2-hydroxy-2-cyclopentenones and 3-amino-2-hydroxy-2-cyclohexenones which are substituted in the 4-position with alkyl containing 1 to 5 carbon atoms. The present invention relates to a method for preparing salts of 3-nitro-1,2 cyclopentanediones which are substituted in the 4-position with an alkyl substituent and in the 5-position with an electron withdrawing group.

SUMMARY OF THE INVENTION

It is therefore the object of this invention to provide a method for preparing salts of 3-nitro-1,2-cyclopentanediones which are substituted in the 4- and 5-positions.

It is another object of the invention to provide a method wherein a nitro olefin compound is utilized as a starting material.

It is a further object to provide a method for preparing 3-nitro-1,2-cyclopentanediones which are substituted in the 4-position with an alkyl substituent and in the 5-position with an electron withdrawing group.

Yet another object is to provide a method for preparing salts of 3-nitro-1,2-cyclopentanediones which are substituted in the 4- position with an alkyl substituent.

BRIEF SUMMARY OF THE INVENTION

These and other objects and advantages are accomplished in accordance with the invention by providing a method for preparing 3-nitro-1,2-cyclopentanedione salts which are substituted in the 4- position with an alkyl substituent and in the 5- position with an electron withdrawing group. The method comprises the addition and spontaneous cyclization reaction of an appropriate nitro olefin with a pyruvate anion. The salts may be neutralized to the nitro diones such as by acidification with an organic or inorganic acid. In another embodiment the salts can be used as intermediates in the preparation of corresponding amino reductones.

DESCRIPTION OF THE PREFERRED EMBODIMENTS

The method of the invention proceeds according to the following general reaction:

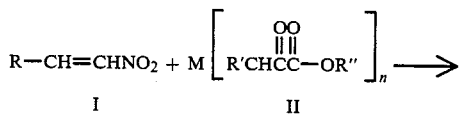

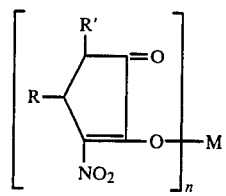

wherein R is alkyl (including straight chain or branched aliphatic moieties or cyclic moieties such as cyclopentyl or cyclohexyl), preferably having from 1 to 18 carbon atoms, which may be unsubstituted or substituted with an aryl group, for example, benzyl or phenethyl, which may itself be substituted with halogens, alkyl, alkoxy, nitro, etc.; R' is an electron withdrawing group such as, for example, cyano, nitro, $-CO_2R'''$ or $-COR^{IV}$, where $R'''$ and $R^{IV}$ are alkyl, preferably having from 1 to 6 carbon atoms; R" is alkyl, preferably having from 1 to 6 carbon atoms; n is 1 or 2; and M is a metallic cation such as Na, K, Li, MgX, (n=1), where X is Cl, Br or I; Ca, Mg (n=2) or the like.

The starting materials for the method of the invention may be commercially available or may be prepared according to reactions which are known in the art. For example, according to one technique, initially an aldehyde such as dodecanal can be condensed with nitromethane in the presence of sodium methoxide such as by adding the sodium methoxide dropwise to a solution of the nitromethane and the aldehyde in a solvent such as methanol to form the sodium salt of the nitro alcohol. Experiments have shown that this reaction is sensitive to excess base and that providing a slight excess of the aldehyde, e.g., about 1%, gave better results. The sodium salt can then be neutralized by treatment with sodium bicarbonate in a solvent such as methylene chloride and the resulting nitro alcohol dehydrated by reaction with methanesulfonyl chloride in the presence of triethylamine, preferably in a molar ratio of nitro alcohol: methanesulfonyl chloride:triethylamine of 1:1.2:2.3, to provide the starting nitro olefin compound.

Generally, equimolar amounts of the nitro olefin (I) and the pyruvate anion (II) are reacted, at reflux, in an organic solvent such as hexane, toluene, tetrahydrofuran, dimethylformamide or the like. Tetrahydrofuran and hexane are preferred because they typically give higher yields. Experiments with 1-nitro-1-tridecene ($C_{11}H_{23}CH=CHNO_2$) and sodium diethyl oxalacetate ($C_2H_5O_2CCH(ONa)CO_2C_2H_5$) have shown that the nitro olefin can be introduced as a methylene chloride solution to a solution of the pyruvate anion in tetrahydrofuran followed by removal of methylene chloride via distillation without any reduction in yield. Thus, the nitro olefin as prepared (after drying) can be used directly in the addition-cyclization reaction without any reduction in yield of the cyclized final product. The reaction is typically carried out for a period of from four to eight hours. Experiments carried out with 1-nitro-1-tridecene and sodium diethyl oxalacetate in tetrahydrofuran showed that a four hour reflux period provided the maximum yield of product. To investigate the effect of concentration on yield, experiments were conducted with 0.25 M, 0.5 M and 1.0 M concentrations (based on theoretical yield) of the reactants mentioned above. The higher concentration gave the highest yield.

The cyclized salt (III) obtained from this reaction can be converted to the corresponding 3-nitro-2-hydroxy-cyclopentanedione by neutralizing the salt such as by acidification with any organic or inorganic acid. In a preferred embodiment wherein R' is —CO₂R''' the cyclized salt (III) is hydrolyzed/decarboxylated under neutral conditions in a two phase water/organic solvent medium. This result was unexpected since attempts to carry out the reaction, using 3-carbethoxy-5-nitro-4-undecyl-1,2-cyclopentanedione, sodium salt, under basic conditions, were not successful, and experiments carried out in acid environment showed that the desired product decomposed at a rate nearly equal to that at which it was formed. The reaction proceeds according to the following equation:

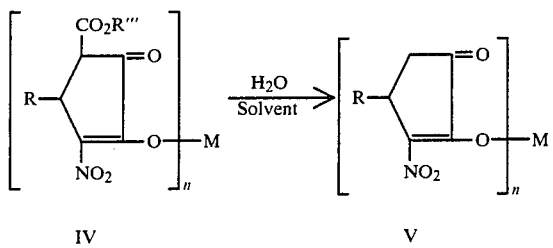

The preferred organic solvent was found to be xylene. The reaction period is typically about twenty hours. Experiments conducted with 3-carbethoxy-5-nitro-4-undecyl-1,2-cyclopentanedione, sodium salt to ascertain the effect on the reaction rate and yield of product, of varying the concentration of the cyclized material indicated that the highest yields were obtained at the lowest concentration (0.12 M). Balancing productivity and yield considerations the optimum concentration of the nitro ester dione, sodium salt was found to be about 0.25 M.

The 3-nitro-4-alkyl-1,2-cyclopentanedione salt (V), which is useful as an intermediate in the preparation of the corresponding amino reductone, is then isolated. Simple cooling of the water/xylene solution results in a highly pure product; however the isolated yield is typically relatively low, i.e., less than 50%. To obtain higher isolation efficiency (% isolated yield/% content yield) the organic solvent phase can be separated from the aqueous phase, held at about 40° C. and added at a moderate rate to a quenching mixture of aqueous sodium chloride, sodium bicarbonate, xylene and isopropanol. The sodium salt of the nitro dione precipitates out in very fine particles which can be recovered by filtration. Alternatively, and preferably, the xylene may be omitted from the quenching mixture in which case the lower aqueous layer can be removed prior to recovering the salt by filtration.

As mentioned previously, the nitro dione salt is useful as an intermediate in the synthesis of 3-amino-4-alkyl-1,2-cyclopentanediones. These compounds can be formed by hydrogenating the salt under standard conditions for reduction of the nitro dione to form the desired amino reductone, such as, for example,

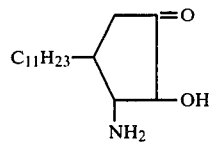

The invention will now be described further in detail with respect to specific preferred embodiments, it being understood that these are illustrative only and the invention is not limited to the materials, process parameters, conditions, etc., recited therein. All parts and percentages are by weight unless otherwise indicated.

EXAMPLE I

A stirred solution of dodecanal (18.43 g., 0.1 mol) and nitromethane (5.98 g., 0.098 mol) in methanol (75 ml) was treated dropwise at room temperature under nitrogen with 25% sodium methoxide in methanol (21.18 g., 0.098 mol) over a 30-minute period without cooling. A precipitate began to form when about 10% of the sodium methoxide solution had been added and the internal temperature rose to 35° C.–40° C. before addition was complete. The mixture was stirred for 15 minutes after addition was complete, cooled to 25° C. and the product collected by filtration. The wet cake was washed by reslurrying with two 50 ml volumes of methanol, sucked dry as possible and dried to give 23.0 g. of the sodium salt of 1-nitro-2-tridecanol, m.p. 176°–200° C.

$C_{13}H_{26}NO_3Na$ requires 58.41% C, 9.80% H, 5.24% N and 8.60% Na. Elemental analysis of the product gave 58.38% C, 10.15% H, 5.18% N and 9.08% Na.

To a solution of sodium bicarbonate (16.8 g.) in water (150 ml) there was added methylene chloride (100 ml) followed by 1-nitro-2-tridecanol, sodium salt (22.63 g., 84.7 mmol) and the mixture stirred at room temperature until a complete solution in methylene chloride was obtained (about 2 hours). The methylene chloride layer was separated, dried with magnesium sulfate and used directly in the next step. Alternatively, some of the nitro alcohol was isolated by evaporating the solvent and allowing the residue to crystallize. A pure sample of nitro alcohol had a melting point of 32°–33.5° C.

$C_{13}H_{27}NO_3$ requires 63.60% C, 11.09% H, and 5.71% N. Elemental analysis of the product found 64.00% C, 10.94% and 5.61% N.

The methylene chloride solution of the nitro alcohol was assayed for nitro alcohol content by diluting 2 ml of the solution to 100 ml with methylene chloride. The UV spectrum of the diluted solution was measured in the range of 350–250 nm and the maximum absorbance in the range 280–275 nm was noted. The concentration of nitro alcohol (1-nitro-2-tridecanol) was then determined using the equation $A = \epsilon c l$ (where A is the absorbance, $\epsilon$ is the molar extinction coefficient, c is the concentration in moles/liter and l is the path length in cm). The value of $\epsilon$ for the nitro alcohol in methylene chloride is 45.2. The solution had an observed A=0.723 and for 1 cm cells, c=3.926 g./liter. Since the original solution was diluted from 2 ml to 100 ml the concentration in the original solution was 196.3 g./liter (95% yield).

The methylene chloride solution of nitro alcohol assayed above (100 ml, 19.63 g., 80.0 mmol) was cooled to 0°–5° C. under nitrogen in a three neck flask fitted with a nitrogen inlet, internal thermometer, reflux condenser and an addition funnel. Methanesulfonyl chloride-98% (12,16 g., 104 mmol) was added over a five minute period and then slow addition of triethylamine (18.6 g., 184 mmol) was begun at a rate adjusted to maintain the internal reaction temperature at 6°–9° C. (about 30 minutes), after which the reaction mixture was stirred at 0°–5° C. for 30 minutes followed by addition of 0.25 M hydrochloric acid (100 ml). The mixture was stirred for 15 minutes and the methylene chloride layer separated and added to 1 M sodium chloride (100 ml). This mixture was stirred for 15 minutes and the methylene chloride again separated and added to a 0.5 M sodium chloride/0.5 M sodium bicarbonate solution (100 ml). The methylene chloride layer was separated after 15 minutes of stirring and to it there was added magnesium sulfate (5 g.). The mixture was stirred for 15 minutes and the magnesium sulfate removed by filtration.

The methylene chloride solution of the nitro olefin (1-nitro-1-tridecene) was assayed by UV spectroscopy by diluting a 1 ml aliquot of the above solution to 100 ml with methylene chloride, further diluting a 1 ml aliquot of diluted solution to 100 ml with methylene chloride and recording the UV spectrum of the final solution from 350–220 nm. The concentration of nitro olefin was calculated by the equation $A = \epsilon cl$ (where A, $\epsilon$, c and l are as defined above). The value of $\epsilon$ for 1-nitro-1-tridecene in methylene chloride is 9307 and A was observed to be 0.707. For 1 cm cells C=17.3 mg./liter. Since the original solution was diluted 1 to 10,000 the concentration in the original solution was 173 g./liter (95.1% yield).

EXAMPLE II

A suspension of 90% sodium diethyl oxalacetate (17.77 g., 76.1 mmol) in tetrahydrofuran (75 ml) was treated dropwise over a 15 minute period with a solution of 1-nitro-1-tridecene (17.30 g., 76.1 mmol) in methylene chloride (about 100 ml). After a complete solution was obtained the reaction mixture was heated in an 80°–90° C. oil bath and the solvent allowed to distill through a 10 cm vigreux column until the boiling point of the distillate reached 63° C. (100–120 ml of the solvent had distilled). Heating at reflux was continued, with no further distillations, for four hours and 150 ml of distilled water were added over a 5 minute period. The reaction mixture was allowed to cool to 30° C. and then cooled in an ice bath to 10° C. A precipitate began to form when the internal temperature reached about 35° C. and the mixture was stirred for one hour at 10° C. before the precipitate was collected by filtration. The solid was washed three times with 100 ml of isopropanol and then dried under vacuum over phosphorous pentoxide. About 23 g. of 3-carbethoxy-5-nitro-4-undecyl-1,2-cyclopentanedione, sodium salt, m.p. 166°–169° C. (dec) were obtained.

$C_{19}H_{30}NO_6Na.\frac{1}{2}H_2O$ requires 56.99% C, 7.80% H, 3.50% N and 5.74% Na. Elemental analysis of the product found 56.92% C, 8.21% H, 3.38% N and 6.14% Na.

A mixture of the sodium salt (31.77 g, dried to constant weight), 3 M hydrochloric acid (150 ml) and xylene (300 ml) was degassed for 10 minutes with a subsurface nitrogen stream, heated to reflux under nitrogen in a bath which was held at 110°–115° C. until two clear solutions were obtained (about 0.5 to 1 hour). The lower aqueous acidic layer was carefully removed and replaced with 5% aqueous sodium chloride (150 ml). The mixture was refluxed for 10 minutes and the lower aqueous layer separated and replaced with 150 ml of the 5% aqueous sodium chloride. The mixture was refluxed for 10 minutes and the lower aqueous layer removed and replaced with 150 ml of distilled water. The reaction mixture was then refluxed with stirring for 20 hours (all operations were carried out under nitrogen with careful exclusion of air). The reaction mixture was cooled to 60° C. and the lower aqueous layer separated followed by cooling the xylene layer to 40° C.

A quenching mixture was prepared by adding sodium chloride (7.50 g) and sodium bicarbonate (7.52 g) to distilled water (150 ml) and the mixture was stirred until a complete solution was obtained (10 minutes) followed by the addition of isopropanol (75 ml). The mixture was degassed for 10 minutes with a sub-surface nitrogen stream and the temperature maintained at 20° C.

The warm xylene solution (40° C.) obtained from the hydrolysis/decarboxylation reaction was added over a period of about 15–30 minutes to the quenching mixture, followed by stirring the mixture at 20° C. for 15 minutes and separation of the lower aqueous layer. The product was collected by filtration on a medium porosity, sintered glass funnel. The crude product was reslurried twice in isopropanol (150 ml) and collected by filtration followed by drying under vacuum to give 20.95 g of yellow 3-nitro-4-undecyl-1,2-cyclopentanedione, sodium salt (81.3% yield) m.p.>250° C. (began to darken at 120° C. but did not form any liquid up to 250° C.). Polarographic analysis by comparison with an analytically pure sample of 3-nitro-4-undecyl-1,2-cyclopentanedione indicated the product to be 96.2% of the nitro dione as the sodium salt.

Although the invention has been described with respect to specific preferred embodiments, it is not intended to be limited thereto but rather those skilled in the art will recognize that variations and modifications may be made therein which are within the spirit of the invention.

What is claimed is:

1. A method for preparing a compound represented by the formula

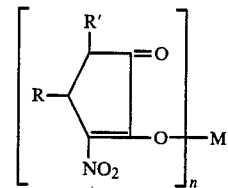

wherein R is alkyl; R' is —CO$_2$R''' wherein R''' is alkyl, n is 1 or 2, and M is a metallic cation comprising the step of reacting a compound represented by the formula R—CH=CHNO$_2$ with a compound represented by the formula

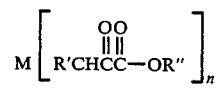

wherein R'' is alkyl.

2. The method as defined in claim 1 wherein R is alkyl having from 1 to 18 carbon atoms.

3. The method as defined in claim 2 wherein R'' is alkyl having from 1 to 6 carbon atoms.

4. The method as defined in claim 1 wherein R is —C$_{11}$H$_{23}$, R' is —CO$_2$C$_2$H$_5$ and M is sodium.

5. The method as defined in claim 1 and further including the step of hydrolyzing and decarboxylating compound I under neutral conditions in a two phase water/organic solvent medium to form a compound represented by the formula
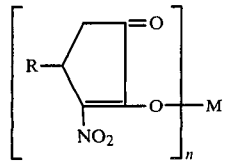
6. The method as defined in claim 5 wherein said organic solvent is xylene.
* * * * *